United States Patent [19]
Verbicky, Jr. et al.

[11] Patent Number: 4,476,309
[45] Date of Patent: Oct. 9, 1984

[54] METHOD FOR MAKING AROMATIC ETHERIMIDES

[75] Inventors: John W. Verbicky, Jr., Scotia; Elbridge A. O'Neil, Jr., Ballston Spa, both of N.Y.

[73] Assignee: General Electric Company, Schenectady, N.Y.

[21] Appl. No.: 476,948

[22] Filed: Mar. 21, 1983

[51] Int. Cl.$^3$ .......................................... C07D 209/48
[52] U.S. Cl. .................................. 548/480; 548/461; 548/476
[58] Field of Search ..................... 548/461, 476, 480

[56] References Cited

U.S. PATENT DOCUMENTS

| | | | |
|---|---|---|---|
| 3,852,242 | 12/1974 | White | 260/47 CZ |
| 3,879,428 | 4/1975 | Heath et al. | 260/346.3 |
| 3,956,320 | 5/1976 | Heath et al. | 260/465 H |
| 3,957,862 | 5/1976 | Heath et al. | 260/520 E |
| 3,965,125 | 6/1976 | Meyers | 260/346.3 |
| 4,202,993 | 5/1980 | Takekoshi | 568/723 |
| 4,257,953 | 5/1981 | Williams et al. | 568/723 |
| 4,273,712 | 6/1981 | Williams | |

*Primary Examiner*—Donald G. Daus
*Assistant Examiner*—M. C. Eakin
*Attorney, Agent, or Firm*—William A. Teoli; James C. Davis, Jr.; James Magee, Jr.

[57] ABSTRACT

A method for making aromatic ether imides is provided by effecting the displacement of reactive radicals on a phthalimide nucleus with a mono- or bis-alkali metal phenoxide in the presence of a nonpolar solvent and a phase transfer catalyst, such as a triorganoborate. The aromatic ether imide made by the present invention are useful intermediates for making aromatic ether anhydrides and aromatic bis(ether anhydrides).

7 Claims, No Drawings

METHOD FOR MAKING AROMATIC ETHERIMIDES

BACKGROUND OF THE INVENTION

The present invention relates to a method for making aromatic etherimides by effecting the condensation of a phenoxide salt with a nuclear-substituted phthalimide in the presence of a nonpolar solvent and a phase transfer catalyst. More particularly, the present invention relates to a method for making an aromatic ether phthalimide or an aromatic bis(ether phthalimide).

Prior to the present invention, methods involving the condensation of an alkali metal phenoxide with a nuclear substituted phthalimide as shown by Heath et al U.S. Pat. Nos. 3,879,428, 3,957,862 and 3,956,320, assigned to the same assignee as the present invention, or Meyers U.S. Pat. No. 3,965,125, were generally based on the use of a dipolar aprotic solvent to facilitate reaction. Those skilled in the art know that it is often economically unattractive to effect the synthesis of various organic materials using dipolar aprotic solvents because such solvents are expensive and often subject to a variety of chemical side reactions which render them useless for recycling.

An improved method for making aromatic etherimides is shown by Williams, U.S. Pat. No. 4,273,712, assigned to the same assignee as the present invention and incorporated herein by reference. The method of Williams is based on the use of a quaternary ammonium salt as a phase transfer catalyst which allows for the use of a nonpolar solvent in place of the dipolar aprotic solvents used in the prior art. Although the method of Williams provides for improved results with respect to the elimination of dipolar aprotic solvents, it has been found that the use of such quaternary ammonium phase transfer catalyst may result in the production of toxic nitrosamines which can interfere with the use of such quaternary ammonium salt catalyst as phase transfer catalysts in industrial methods for making aromatic etherimides.

The present invention is based on the discovery that an effective amount of a triorganoborate of the formula,

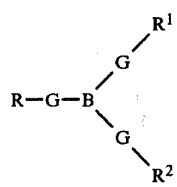

(1)

where R, $R^1$ and $R^2$ are selected from monovalent $C_{(1-13)}$ hydrocarbons radicals and substituted $C_{(1-13)}$ hydrocarbon radicals and G is a divalent radical selected from oxygen and sulfur, can be used as phase transfer catalysts for making aromatic etherimides of the formula,

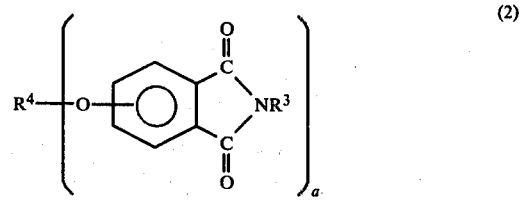

(2)

In addition to avoiding the generation of nitrosamines, the use of the triorganoborates of formula (1) as phase transfer catalyst for aromatic etherimide formation does not require the use of a dipolar aprotic solvent. Reaction can be effected between an alkali metal phenoxide salt or diphenoxide salt, and a nuclear substituted phthalimide in a nonpolar organic solvent, where $R^3$ is a monovalent radical selected from hydrogen, a $C_{(1-8)}$ alkyl radical and $C_{(6-13)}$ aryl radical, $R^4$ is a $C_{(6-30)}$ aromatic organic radical, and a is an integer equal to 1 or 2, and when a is 1, $R^4$ is monovalent and when a is 2, $R^4$ is divalent.

STATEMENT OF THE INVENTION

There is provided by the present invention, a method for making aromatic etherimide of formula (2), which comprises, (A) heating a substituted phthalimide of the formula,

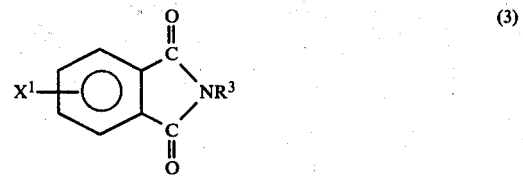

(3)

and an alkali metal phenoxide salt of the formula,

$(R^4—OM)_a$ (4)

in the presence of a nonpolar organic solvent and an amount of a triorganoborate of formula (1) which is effective as a phase transfer catalyst, (B) agitating the resulting mixture with a precipitating or extractive organic solvent for the resulting bisimide or allowing the mixture to cool and (C) recovering the bisimide from the mixture of (B), where $R^3$ and $R^4$ and a are as previously defined, M is an alkali metal ion and $X^1$ is a radical selected from nitro and halo.

Radicals included by R, $R^1$ and $R^2$ are, for example, a $C_{(1-8)}$ alkyl radical such as methyl, ethyl, propyl, butyl, pentyl, hexyl, etc., a $C_{(6-13)}$ aromatic hydrocarbon radical such as phenyl, tolyl, xylyl, naphthyl, etc.; halogenated $C_{(1-13)}$ hydrocarbon radicals for example chloroethyl, chlorophenyl, etc. Radicals included by $R^3$ are, for example, phenyl, tolyl, xylyl, naphthyl, chlorophenyl, bromonaphthyl, etc. Radicals included by $R^4$ are the aforementioned monovalent aromatic radicals included by $R^3$ and divalent aromatic radicals, such as phenylene, tolylene, naphthylene, and more particularly

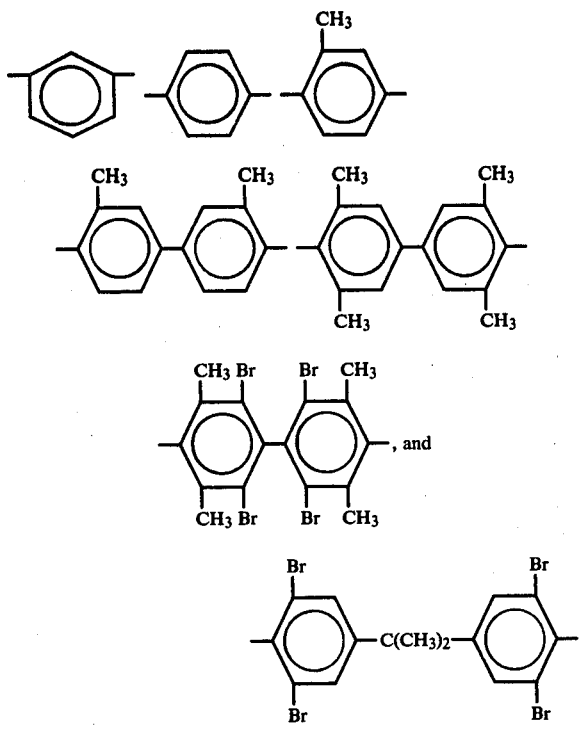

and divalent organic radicals of the general formula,

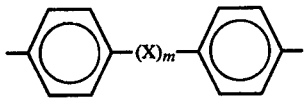

where X is a member selected from the class consisting of divalent radicals of the formula,

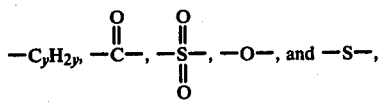

where m is 0 or 1, y is a whole number from 1 to 5. M is more particularly sodium, potassium, lithium, rubidium, etc.;

Included by the substituted phthalimides of formula (3), are for example,
4-nitro,N-phenylphthalimide;
3-nitro,N-phenylphthalimide;
4-nitro,N-methylphthalimide;
3-nitro,N-methylphthalimide;
4-fluoro,N-methylphthalimide;
3-fluoro,N-methylphthalimide;
4-chloro,N-methylphthalimide;
3-chloro,N-methylphthalimide, etc.

Included by the triorganoborates or borate esters of formula (1) are, for example,
tri-t-butylborate;
diethylphenylborate;
triethylborate;
tri-n-butylborate;
triphenylborate; etc.

Triorganoborates included within formula (1) are further shown in Kirk Othmer, Encyclopedia of Chemical Technology, Vol. 4, pages 111 to 123, Third Edition, (1980), John Wiley and Sons, New York.

The alkali metal salts of formula (4) can be made by various procedures, including the flash evaporation of bisphenoxide alkali metal salt hydrate or an aqueous slurry thereof, as shown by Takekoshi, U.S. Pat. No. 4,202,993, or by azeotroping water from an aqueous mixture of bisphenoxide alkali metal salt and toluene as shown by Williams, III et al, U.S. Pat. No. 4,257,953. Additional procedures are shown in White, U.S. Pat. No. 3,852,242, assigned to the same assignee as the present invention.

Some of the alkali metal salts of the abovedescribed alkali phenoxides of formula (4) are sodium and potassium salt phenols, such as phenol, cresol, naphthol, etc.; dihydric phenols, for example.
2,2-bis(2-hydroxyphenyl)propane;
2,4'-dihydroxydiphenylmethane;
bis(2-hydroxydiphenyl)methane;
2,2-bis(4-hydroxyphenyl)propane, hereinafter identified as "bisphenol-A" or "BPA";
1,1-bis(4-hydroxyphenyl)ethane;
1,1-bis(4-hydroxyphenyl)propane;
2,2-bis(4-hydroxyphenyl)pentane;
3,3-bis(4-hydroxyphenyl)pentane;
4,4'-dihydroxybiphenyl;
4,4'-dihydroxy3,3,5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenylsulfoxide;
4,4'-dihydroxydiphenylsulfide;
hydroquinone;
resorcinol;
3,4'-dihydroxydiphenylmethane;
4,4'-dihydroxybenzophenone; and
4,4'-dihydroxydiphenylether.

In the practice of the invention, reaction is effected between the substituted phthalimide and the phenoxide salt, which hereinafter will signify either the mono- or dihydric phenol salt in the presence of a nonpolar solvent and an effective amount of the triorganoborate, followed by the recovery of the resulting "ether phthalimide" which hereinafter can signify either aromatic ether phthalimide, or aromatic bis(ether phthalimide). It is preferred to effect reaction under substantially anhydrous conditions, although small amounts of moisture can be tolerated.

Temperatures at which reaction between the phenoxide salt and the substituted phthalimide can be effected are in the range of about between 25° C. to 150° C. and preferably a temperature between 100° C.-120° C. Any nonpolar organic solvent which does not react with the reactants during the formation of the ether phthalimide can be used in the reaction. Some of the nonpolar organic solvents are, for example, toluene benzene, chlorobenzene, xylene, tetrahydrofuran, acetonitrile. octane, etc.

Experience has shown that the reaction can best be run using a solids concentration in the range of between about 15% to 50% by weight of solids, based on the total weight of reaction mixture, and preferably from between about 20 to 40% by weight. Preferably, equivalent amounts of the phenoxide salt and a substituted phthalimide can be used, while higher or lower amounts of either reactant will not substantially interfere with the formation of the desired ether phthalimide. In preparing the aromatic bis(ether phthalimide) there is preferably used about 2 moles of the substituted phthalimide, per mole of the bisphenoxide salt. The triorganoborate can be utilized at from 0.03 to 0.40 part of triorganoborate, per part of alkali bisphenoxide and preferably from 0.040 to 0.05 part, per part of alkali bisphenoxide.

The ether phthalimide can be recovered from the reaction mixture by a variety of procedures. One procedure, for example, can be by allowing the reaction mixture to cool, followed by recovery of the ether phthalimide by filtration. It is preferred, however, because of the partial solubility of the ether phthalimide in various nonpolar organic solvents, to precipitate the ether phthalimide by use of a precipitating solvent, for example, methanol, followed again by a standard recovery technique, such as filtration. Alternatively, the ether phthalimide can be extracted from the reaction mixture with a better solvent such as methylene chloride, chloroform, etc., washed with water to effect removal of the inorganic salts, and recovered by the removal of the organic solvent under reduced pressure.

Experience has shown that the triorganoborates and by-products of the reaction can be recycled directly for further use in the production of etherphthalimide in accordance with the practice of the invention. For example, in the situation where the reaction mixture is allowed to cool to room temperature to effect the separation of ether phthalimide, the filtrate can be reused as a source of the triorganoborate and the nonpolar organic solvent. In instances where a precipitating solvent is employed to effect the separation of ether phthalimide, the filtrate can be evaporated to dryness to recover the triorganoborate which can be recycled.

In order that those skilled in the art will be better able to practice the invention, the following example is given by way of illustration and not by way of limitation. All parts are by weight.

EXAMPLE 1

The anhydrous salt of disodium bisphenol-A was prepared in accordance with the method shown in Takekoshi, U.S. Pat. No. 4,202,993, assigned to the same assignee as the present invention and incorporated herein by reference. There was added under ambient conditions with stirring 50 microliters of tri-t-butylborate to a slurry of 1.5 grams of the anhydrous salt of disodium bisphenol-A and 2.27 grams of N-methyl-4-nitrophthalimide in 8 ml of toluene. The resulting reaction mixture was then heated with stirring to reflux for 30 minutes. There was obtained a 77% yield of an ether phthalimide having the formula,

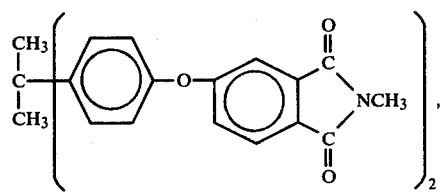

based on reverse phase liquid chromatography using ortho-terphenyl as an internal standard.

The same reaction was repeated except, that in place of tri-t-butylborate, there was utilized tri-n-butylborate. The reaction mixture was stirred and refluxed for 60 minutes. There was obtained a 77.5% yield of the same bisphenol-bisimide using reverse phase liquid chromatography as previously described.

The above results show that the method of the present invention provides a significant advance over the procedures shown in the prior art in view of the elimination of potential toxic by-products such as nitrosamines while providing for satisfactory yields of imides or bisimides.

Although the above examples are directed to only a few of the very many variables which are included within the scope of the present invention, it should be understood that the present invention is directed to the use of a much broader variety of phenols and bisphenols, nitro or halophthalimides and triorganoborates as shown in the description preceding these examples.

What we claim as new and desire to secure by Letters Patent of the United States is:

1. A method for making aromatic etherimide of the formula

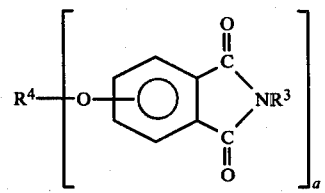

which comprises, (A) heating a substituted phthalimide of the formula,

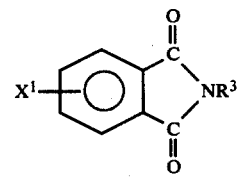

and an alkali metal phenoxide salt of the formula, $(R^4—OM)_a$ in the presence of a nonpolar organic solvent and from 0.03 to 0.40 part per part of the alkali metal phenoxide salt, if a triorganoborate having the formula

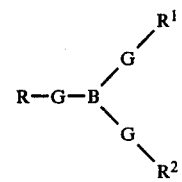

(B) agitating the resulting mixture with a precipitating or extractive organic solvent for the resulting bisimide or allowing the mixture to cool and (C) recovering the bisimide from the mixture of (B), where R, $R^1$ and $R^2$ are selected from monovalent $C_{(1-13)}$ hydrocarbon groups and substituted $C_{(1-13)}$ monovalent hydrocarbon groups, $R^3$ is a monovalent group selected from the class consisting of hydrogen, a $C_{(1-8)}$ alkyl radical and a $C_{(6-13)}$ aryl group, $R^4$ is an aromatic group selected from the group consisting of a $C_{(6-30)}$ aromatic carbocyclic group, a halogenated C_{(6-30)} aromatic carbocyclic group and an alkylated C_{(6-30)} carbocyclic group and a divalent organic group of the formula,

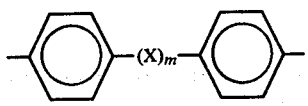

where X is a member selected from the group consisting of divalent groups of the formula,

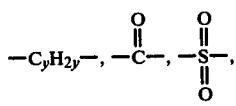

—O—, and —S—, m is 0 or 1, y is a whole number from 1 to 5, G is a divalent group selected from oxygen and sulfur, M is an alkali metal ion, $X^1$ is a group selected from nitro and halo, and a is an integer equal to 1 or 2, and when a is 1, $R^4$ is monovalent and when a is 2, $R^4$ is divalent.

2. A method in accordance with claim 1, where the triorganoborate is a trialkylborate.

3. A method in accordance with claim 1, where the triorganoborate is tri-t-butylborate.

4. A method in accordance with claim 1, where the triorganoborate is tri-n-butylborate.

5. A method in accordance with claim 1, where the phenoxide salt is a disodium salt of bisphenol-A.

6. A method in accordance with claim 1, where the substituted phthalimide is N-methyl-4-nitrophthalimide.

7. A method in accordance with claim 1, where the nonpolar organic solvent is toluene.

* * * * *